(12) United States Patent
Gundlapalli et al.

(10) Patent No.: US 6,962,607 B2
(45) Date of Patent: Nov. 8, 2005

(54) JOINT REPLACEMENT PROSTHESIS COMPONENT WITH NON LINEAR INSERT

(75) Inventors: Rama Rao V. Gundlapalli, Leesburg, IN (US); Mark Heldreth, Mentone, IN (US); Albert Burstein, Sarasota, FL (US)

(73) Assignee: Depuy Products, Inc., Warsaw, IN (US)

( * ) Notice: Subject to any disclaimer, the term of this patent is extended or adjusted under 35 U.S.C. 154(b) by 158 days.

(21) Appl. No.: 10/154,869

(22) Filed: May 24, 2002

(65) Prior Publication Data

US 2003/0009231 A1 Jan. 9, 2003

Related U.S. Application Data

(60) Provisional application No. 60/302,098, filed on Jun. 30, 2001.

(51) Int. Cl.[7] .................................................. A61F 2/38
(52) U.S. Cl. .................................................. 623/22.29
(58) Field of Search ................ 623/18.11, 19.11–19.13, 623/20.11–20.13, 20.14–20.15, 20.21–20.29, 20.31–20.36, 21.15–21.19, 23.39–23.41

(56) References Cited

U.S. PATENT DOCUMENTS

| | | | |
|---|---|---|---|
| 4,298,992 A | 11/1981 | Burstein et al. | |
| 4,501,031 A | 2/1985 | McDaniel et al. | |
| 4,959,071 A | * 9/1990 | Brown et al. ............ | 623/20.27 |
| 4,997,445 A | 3/1991 | Hodorek | |
| 5,007,933 A | 4/1991 | Sidebotham et al. | |
| 5,139,521 A | 8/1992 | Schelhas | |
| 5,176,684 A | 1/1993 | Ferrante et al. | |
| 5,282,866 A | 2/1994 | Cohen et al. | |
| 5,370,699 A | 12/1994 | Hood et al. | |
| 5,405,396 A | 4/1995 | Heldreth et al. | |
| 5,413,604 A | 5/1995 | Hodge | |
| 5,549,686 A | 8/1996 | Johnson et al. | |

(Continued)

FOREIGN PATENT DOCUMENTS

| | | |
|---|---|---|
| DE | 4434806 A1 | 4/1996 |
| EP | 0724868 A1 | 7/1996 |

(Continued)

OTHER PUBLICATIONS

EPO Search Report (App. No. 02254480.3) dated Nov. 7, 2002.

(Continued)

*Primary Examiner*—Kevin Shaver
*Assistant Examiner*—Michael B. Priddy

(57) ABSTRACT

According to one embodiment of the present invention, there is provided a joint prosthesis (10) having a first component (12) for cooperation with a first long bone (14) and a second component (16) for cooperation with a second long bone (20). The joint prosthesis (10) further includes a bearing component (22) positionable between the first component (12) and the second component (16) and cooperable with the first component (12) and the second component (16). The bearing component (22) includes a reinforcing component (36) having a first portion (54) defining a first centerline (50) and having a second portion (56) defining a second centerline (52). The first centerline (50) and the second centerline (52) are non-coincidental. The bearing component (22) includes a polymeric material (112) surrounding the reinforcing component (36) and molded to the reinforcing component (36). The bearing component (22) defines a first peripheral region (34) adjacent the first portion (54) of the reinforcing component (36) and a second peripheral region (82) adjacent the second portion (56) of the reinforcing component(36). The first peripheral region (34) cooperates with first component (12) and the second peripheral region (82) cooperates with the second component (16).

3 Claims, 19 Drawing Sheets

U.S. PATENT DOCUMENTS

| | | |
|---|---|---|
| 5,577,368 A | 11/1996 | Hamilton et al. |
| 5,609,643 A | 3/1997 | Colleran et al. |
| 5,658,344 A | 8/1997 | Hurlburt |
| 5,683,470 A | 11/1997 | Johnson et al. |
| 5,702,460 A | 12/1997 | Carls et al. |
| 5,755,808 A | 5/1998 | DeCarlo et al. |
| 5,776,200 A | 7/1998 | Johnson et al. |
| 5,824,103 A | 10/1998 | Williams |
| 5,830,396 A | 11/1998 | Higgins et al. |
| 5,871,546 A | 2/1999 | Colleran et al. |
| 5,989,472 A | 11/1999 | Ashby et al. |
| 5,997,577 A | 12/1999 | Herrington et al. |
| 6,004,351 A | 12/1999 | Tomita et al. |
| 6,004,352 A | 12/1999 | Buni |
| 6,017,975 A | 1/2000 | Saum et al. |
| 6,123,728 A | 9/2000 | Brosnahan et al. |
| 6,123,729 A | 9/2000 | Insall et al. |
| 6,125,255 A | 9/2000 | Litman et al. |
| 6,126,692 A | 10/2000 | Robie et al. |
| 6,165,223 A * | 12/2000 | Metzger et al. .......... 623/20.27 |
| 6,228,900 B1 | 5/2001 | Shen et al. |
| 6,242,507 B1 | 6/2001 | Saum et al. |
| 6,475,241 B2 * | 11/2002 | Pappas .................... 623/20.29 |

FOREIGN PATENT DOCUMENTS

| | | |
|---|---|---|
| EP | 0963824 A | 12/1999 |
| EP | 1133959 A1 | 9/2001 |
| EP | 1270187 A3 | 2/2004 |
| FR | 2760352 | 10/1997 |

OTHER PUBLICATIONS

EPO Search Report (App. No. 02254480.3) dated Oct. 22, 2003.

* cited by examiner

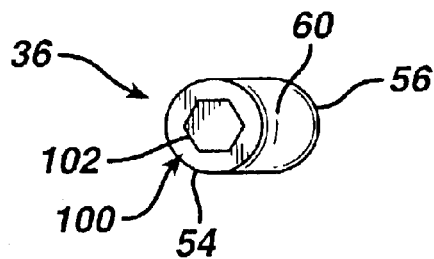
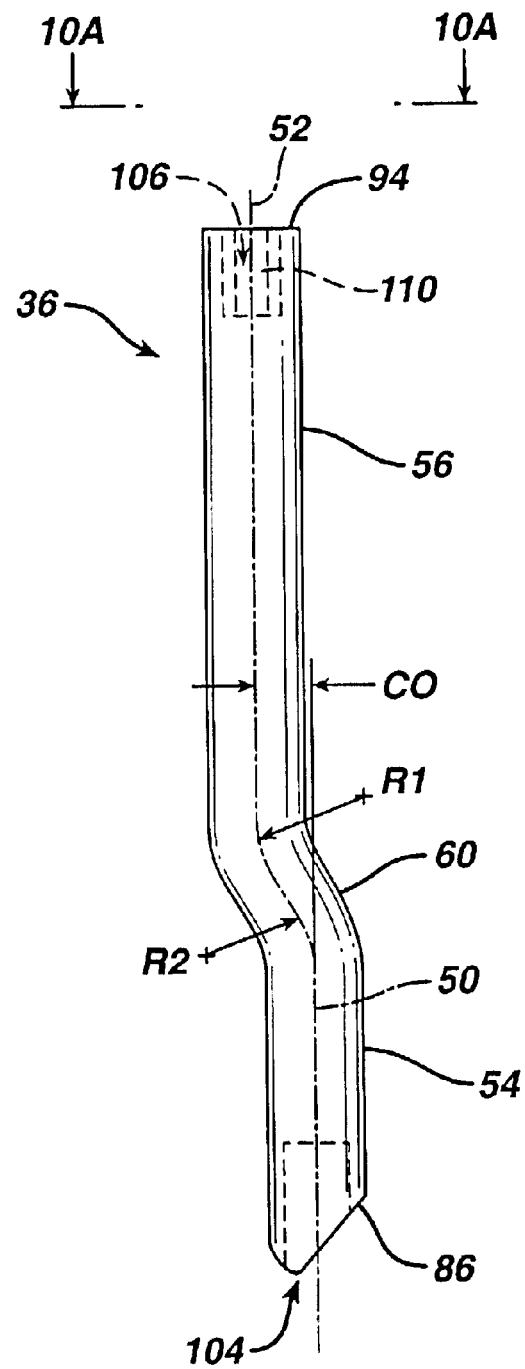

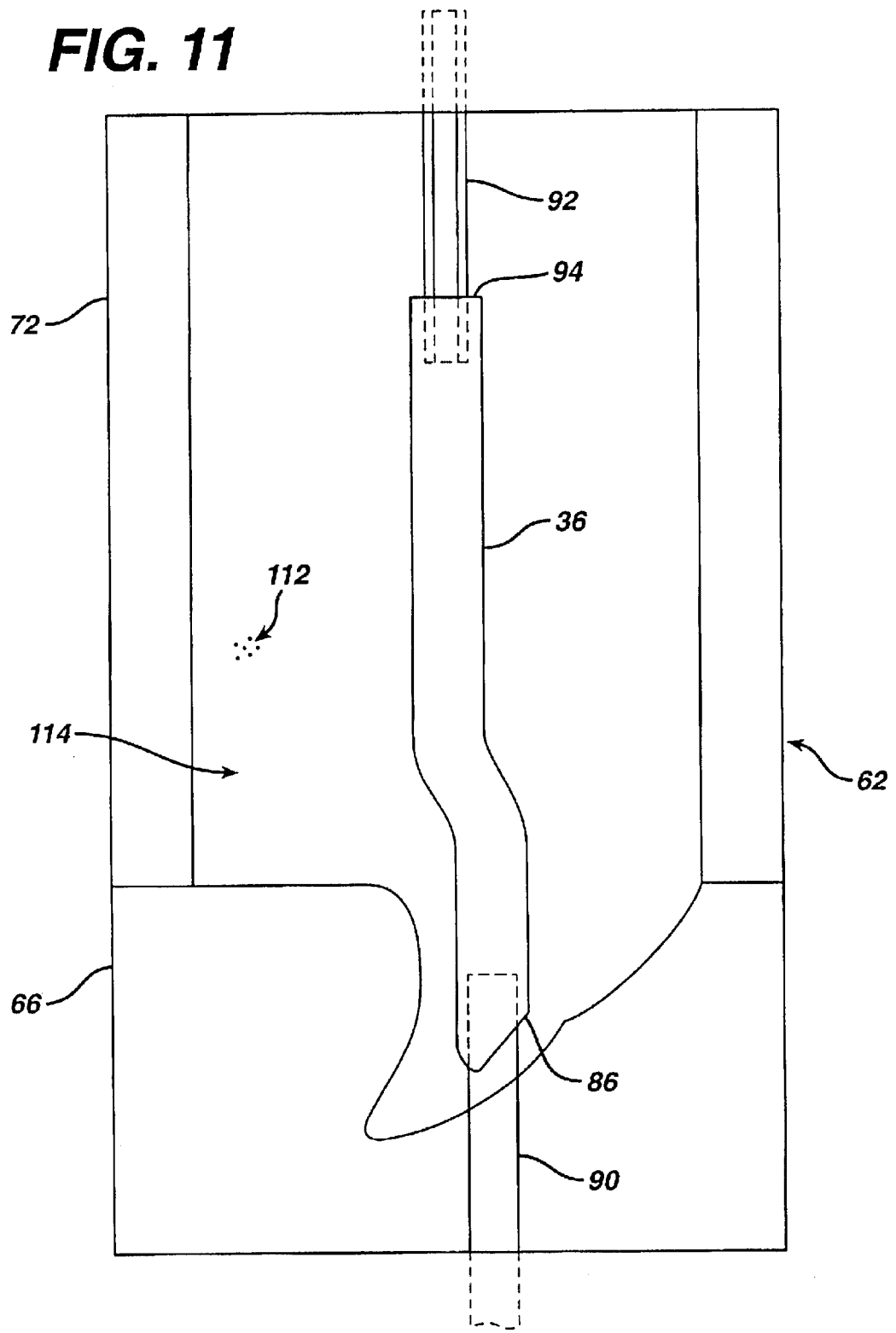

JOINT REPLACEMENT PROSTHESIS COMPONENT WITH NON LINEAR INSERT

CROSS REFERENCE TO U.S. PROVISIONAL PATENT APPLICATION

This application is a Utility Application based upon U.S. Provisional Patent Application, Ser. No. 60/302,098 filed Jun. 30, 2001, entitled JOINT REPLACEMENT PROSTHESIS COMPONENT WITH NON LINEAR INSERT.

CROSS-REFERENCE TO RELATED APPLICATIONS

Cross reference is made to the following applications:

DEP 677 titled "JOINT PROSTHESIS MOLDING METHOD AND DIE FOR PREFORMING THE SAME" and DEP 678 titled "SURFACE STERILIZABLE JOINT REPLACEMENT PROSTHESIS COMPONENT WITH INSERT" filed concurrently herewith which are incorporated herein by reference.

TECHNICAL FIELD OF THE INVENTION

The present invention relates generally to the field of orthopaedics, and more particularly, to an implant for use in joint arthroplasty.

BACKGROUND OF THE INVENTION

The invention relates to joint prostheses. More particularly, the invention is directed to tibial components of knee joint prostheses that can be configured to be either rotatable or non-rotatable.

Joint replacement surgery is quite common and it enables many individuals to function normally when it otherwise would not be possible to do so. Artificial joints usually comprise metallic, ceramic and/or plastic components that are fixed to existing bone.

Knee arthroplasty is a well known surgical procedure by which a diseased and/or damaged natural knee joint is replaced with a prosthetic knee joint. A typical knee prosthesis includes a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert.

The tibial plateau is mounted within the tibia of a patient. Typically, the tibial bearing insert, which is usually made of ultra high molecular weight polyethylene (UHMWPE), is mounted upon the superior surface of the tibial plateau. The geometry and structure of the tibial bearing insert varies depending upon the needs and joint condition of a patient. Some tibial bearing inserts are designed to be used with joint prostheses that are implanted during procedures that retain the cruciate ligaments. Others are implanted after removal of the cruciate ligaments, and are thus structured to compensate for the loss of these ligaments. Yet other tibial bearing inserts are used with prostheses that provide enhanced stabilization to the knee joint.

Recent total knee prostheses have been designed, which allow for some freedom of rotation between the femur and the tibia. To allow for this rotational motion, tibial bearing inserts have been designed which allow for rotation of the insert on the tibial tray or plateau implant. Typically, the tibial bearing inserts have a central stem which rotationally engages centrally in the tibial stem of the tibial tray implant thereby providing for the rotational motion. Typically, there are no rotational constraints between the tibial tray implant and the tibial bearing insert. Frequently, during total knee arthroplasty, the posterior cruciate ligaments are sacrificed and a substitute for the posterior cruciate ligaments are required. Orthopaedic implants for total knee arthroplasty have been developed which provide for the substitution of the posterior cruciate ligament. Examples of such implants include the PFC Sigma RP as described in U.S. Pat. No. 4,298,992 incorporated herein by reference and the LCS Complete total knee prosthesis, both of which are sold by DePuy Orthopaedics, Inc., Warsaw, Ind.

These total knee prostheses are designed with tibial components and femoral components which have in conjunction with their articulating surface, a spine and cam mechanism, which is used as a posterior cruciate substituting feature when the posterior cruciate of the knee is sacrificed.

Such total knee replacement prostheses, which include a spine and cam mechanism, typically contain tibial bearing components manufactured from suitable plastic, usually UHMWPE. One such construction use for a class of total knee replacement prosthesis, which are known as constrained prosthesis often incorporate metal reinforcement rods in the construction of the plastic bearing component. The bearing insert is constructed so that the metal rod lies within the bearing, and thus provides additional support for the central spine element of the bearing. Such components are typically manufactured by machining or molding the bearing component, drilling a central hole, and press fitting the reinforcing metal rod. An example of such a component is described in U.S. Pat. No. 5,007,933 Sidebotham, et al., hereby incorporated in its entirety by reference.

In order to allow for desired kinematics of the knee during a full range of motion, the spine and cam mechanism on the tibial bearing insert may be placed in a suitable position, preferably anterior to the center line of the insert in the anterior/posterior direction. Designs of tibial inserts are available to help reconstruct knees where the stabilizing soft tissue compromises have been made or occurred due to various reasons. In such cases, the tibial bearing inserts are required to experience greater loads in the anterior/posterior and the medial/lateral directions. The constrained inserts may be reinforced with a metal rod, as mentioned earlier, to help distribute the loads experienced by the spine of the polyethylene tibial bearing.

Total knee joint prostheses have been designed with the spine and cam mechanisms on the tibial bearing insert placed in a position such that the central axis of the distal stem portion of the insert that engages the tibial tray and the axis of the superior spine portion that engages the cam of the femoral component are not necessarily collinear.

Unfortunately, this design does not allow for a straight rod, commonly employed for reinforcement of tibial bearing inserts, to be used.

It should be appreciated that a first rod could be inserted inside the spine and a second rod could be inserted in the stem of the tibial tray portion of the bearing insert. However, the load on the first rod would be transferred through the polymer portion of the insert to the second rod. The polymer strength would then limit the load carrying capacity of this configuration. Such a configuration may not provide the required strength to sufficiently support and reinforce the spine.

The present invention is directed to providing a tibial bearing insert with a metal reinforcing rod at the spine to withstand the loads of the knee prosthesis in the anterior/posterior and medial/lateral directions when the central axis of the distal stem portion of the insert and the axis of the superior spine portion are not necessarily co-linear.

SUMMARY OF THE INVENTION

The present invention is directed to an improved joint prosthesis for total knee replacement, which includes a spine and cam mechanism. The cam mechanism being on the femoral component and the spine being on the tibial bearing insert. The mechanism is capable of withstanding the greater loads experienced in the anterior/posterior and medial/lateral direction caused by the compromised posterior cruciate and/or collateral ligaments present during total knee arthroplasty.

The spine on the tibial bearing insert according to the present invention is placed anterior to the centerline of the insert in the anterior posterior direction. Therefore, the distal stem portion of the insert, which rotationally engages the tibial tray and the superior spine portion, which engages the cam of the femoral component, are not necessarily collinear. The tibial bearing insert of the present invention thus includes a rod placed internal to the tibial bearing insert which includes such an offset feature. The knee prosthesis of the present invention thus includes a first component including a first portion on a first center line and a second portion on a second center line such that the first portion may rotationally engage the tibial tray and the second portion may be cooperating with the cam mechanism in the femoral component of the knee prosthesis.

According to one embodiment of the present invention, there is provided a joint prosthesis having a first component for cooperation with a first long bone and a second component for cooperation with a second long bone.

The joint prosthesis further includes a bearing component positionable between the first component and the second component and cooperable with the first component and the second component. The bearing component includes a reinforcing component having a first portion defining a first centerline and having a second portion defining a second centerline. The first centerline and the second centerline are non-coincidental. The bearing component includes a polymeric material surrounding the reinforcing component and molded to the reinforcing component. The bearing component defines a first peripheral region adjacent the first portion of the reinforcing component and a second peripheral region adjacent the second portion of the reinforcing component. The first peripheral region cooperates with first component and the second peripheral region cooperates with the second component.

According to another embodiment of the present invention a joint prosthesis is provided. The joint prosthesis includes a first component for cooperation with a first long bone and a second component for cooperation with a second long bone. The joint prosthesis also includes a bearing component positionable between the first component and the second component and cooperable with the first component and the second component. The bearing component has a reinforcing component including an arcuate portion, a first end portion extending from the arcuate portion, and a second end portion extending from the arcuate portion. The bearing component includes a polymeric material substantially surrounding at least the arcuate portion of the reinforcing component and molded to the arcuate portion. The bearing component has a first peripheral region adjacent the first end portion of the reinforcing component and a second peripheral region adjacent the second end portion of the reinforcing component. The first peripheral region cooperates with the first component and the second peripheral region cooperates with the second component.

According to a further embodiment of the present invention a joint prosthesis is provided. The joint prosthesis includes a joint prosthesis includes a first component for cooperation with a first long bone and a second component for cooperation with a second long bone. The joint prosthesis also includes a bearing component positionable between the first component and the second component and cooperable with the first component and the second component. The bearing component includes a reinforcing component having a first portion defining a first centerline and having a second portion defining a second centerline. The first centerline and the second centerline are non-coincidental. The bearing component also includes a polymeric material substantially surrounding at least a portion of the reinforcing component and molded to the reinforcing component. The bearing component defines a first peripheral region adjacent the first portion of the reinforcing component and defines a second peripheral region adjacent the second portion of the reinforcing component. The first peripheral region cooperates with the first component and the second peripheral region cooperates with the second component.

According to yet another embodiment of the present invention a knee prosthesis is provided. The knee prosthesis includes a femoral component for attachment to a femur and a tibial tray for attachment to a tibia. The knee prosthesis also includes a bearing component positionable between the femoral component and the tibial tray for cooperation with the femoral component and the tibia tray. The bearing component includes a first component having a first portion defining a first centerline and having a second portion defining a second centerline. The first centerline and the second centerline are non-coincidental. The bearing component further includes a polymeric material substantially surrounding the first component and molded to the first component. The bearing component defines a first peripheral region adjacent the first portion of the first component and defines a second peripheral region adjacent the second portion of the first component. The first peripheral region cooperates with the femoral component and the second peripheral region cooperates with the tibial tray.

According to another embodiment of the present invention a bearing component is provided. The bearing component is for use in a joint prosthesis and is cooperable with a first component for implantation into a first long bone and cooperable with a second component for implantation onto a second long bone. The bearing component includes a reinforcing component having a first portion defining a first centerline and having a second portion defining a second centerline. The first centerline and the second centerline are non-coincidental. The bearing component also includes a polymeric material substantially surrounding the reinforcing component and molded to the bearing component. The bearing component defines a first peripheral region adjacent the first portion of the reinforcing component and defines a second peripheral region adjacent the second portion of the reinforcing component. The first peripheral region cooperating with the first component and the second peripheral region cooperating with the second component.

If a total knee prosthesis requires removal from the patient and replacement with a new prosthesis, such replacement prosthesis typically engage further into the medullary canals of the femur and tibia. Such prostheses are called revision prostheses. During the prosthesis replacement, posterior cruciate ligaments are more often sacrificed than in an initial or primary total knee arthroplasty. Currently no revision tibial bearing inserts with rotational features include a spine that has a centerline not aligned with the center of the distal stem portion of the insert that rotationally engages the tibial tray.

Attempts have been made to reinforce polyethylene bearings. One such attempt is that as shown in U.S. Pat. No. 5,989,472 Ashby, et al, incorporated herein by reference. The polyethylene bearing in Ashby includes a reinforcement feature for bone attachment. The reinforcement feature is to assist in eliminating motion between the polyethylene and the metal backing.

Another attempt at reinforcing a polyethylene bearing is described in U.S. Pat. No. 4,997,445 to Hodoreck incorporated herein by reference. This patent describes a metal backed prosthesis implant with enhanced bonding of polyethylene to the metal base. An example of such a component is described in U.S. Pat. No. 5,007,933 Sidebotham, et al. hereby incorporated in its entirety by reference.

The technical advantages of the present invention include the ability to allow for the desired kinematics of the knee during a full range of motion for patients in whom the cruciate ligaments have either been severely damaged, removed, or sacrificed. In such conditions the femoral and tibial components of the knee prosthesis need to be constrained with respect to each other by use of, for example, a spine and cam mechanism.

According to one aspect of the present invention, the support or reinforcing member may be placed within a molding die and a tibial bearing insert may be molded including the non-linear support rod.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 10 is a plan view of a reinforcing rod for use with the bearing component for an embodiment of the prosthesis of the present invention;

FIG. 10A is a view of the reinforcing rod of FIG. 10 along the line 10A—10A in the direction of the arrows;

FIG. 11 is a plan view of the reinforcing rod of FIG. 10 located in a molding die for use in manufacturing the bearing component for the prosthesis of the present invention;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
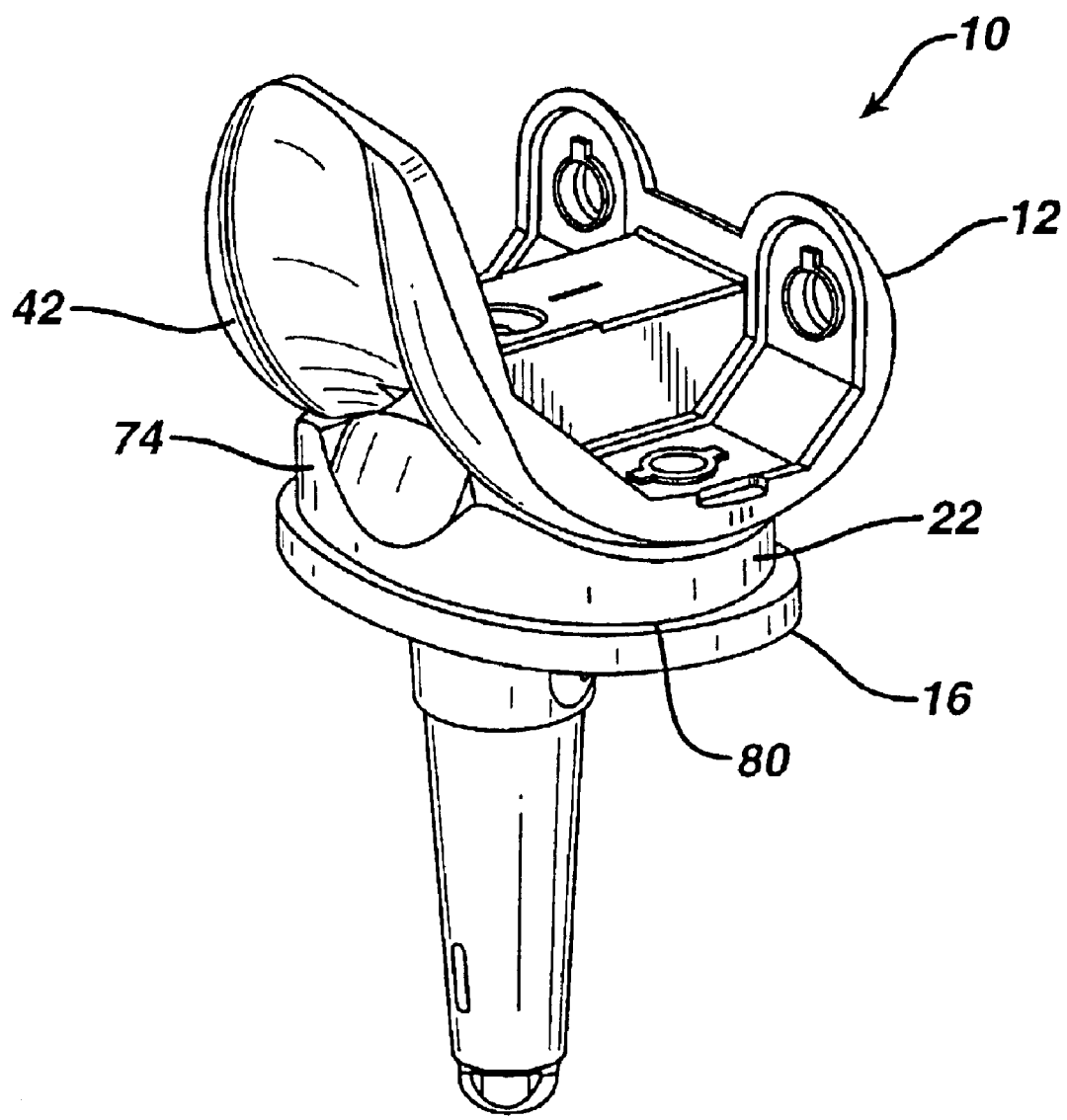
FIG. 1 is a perspective view of the knee system including the bearing component of the present invention showing the femoral component and the tibial component with the tibial bearing showing the knee system in extension.
Figure 2:
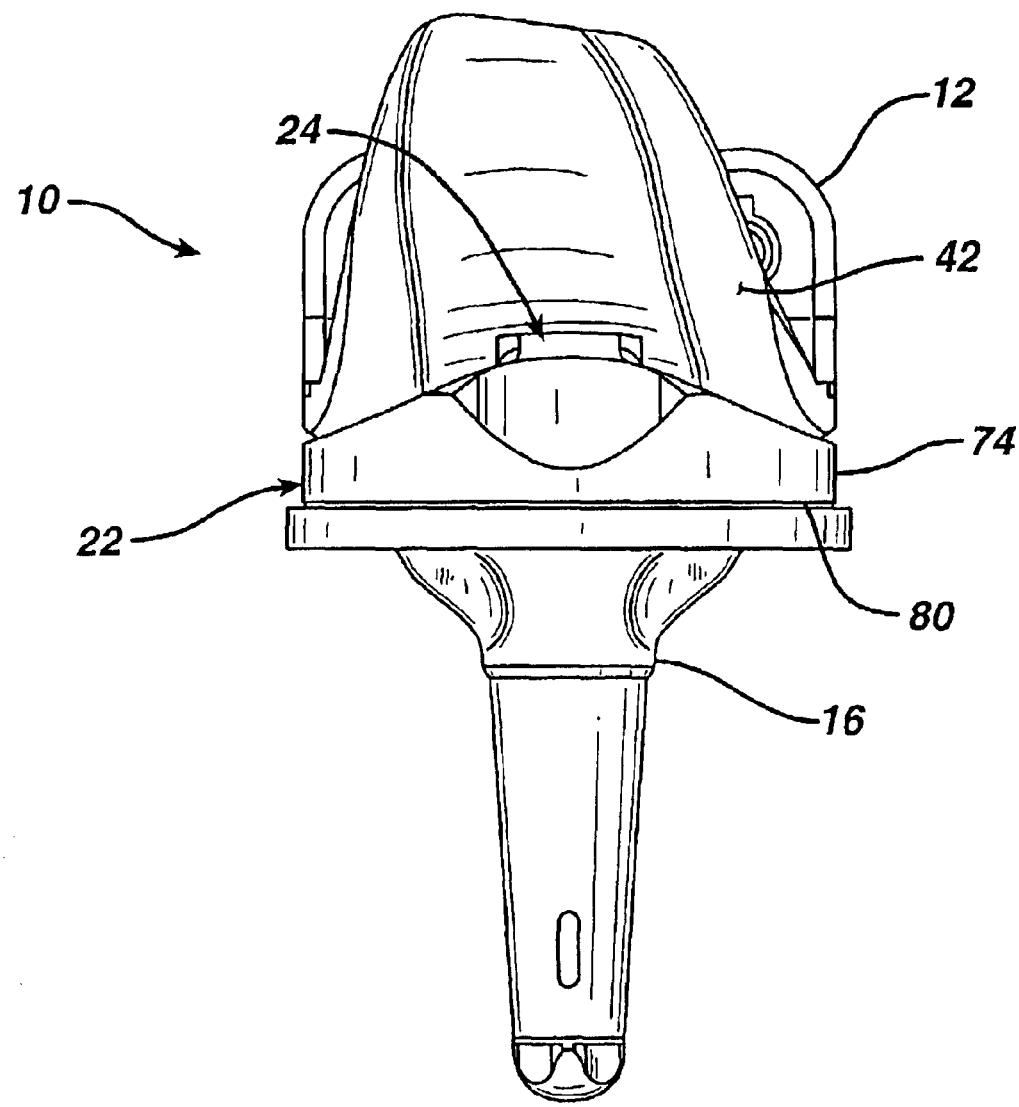
FIG. 2 is an elevation view from the anterior of FIG. 1.
Figure 3:
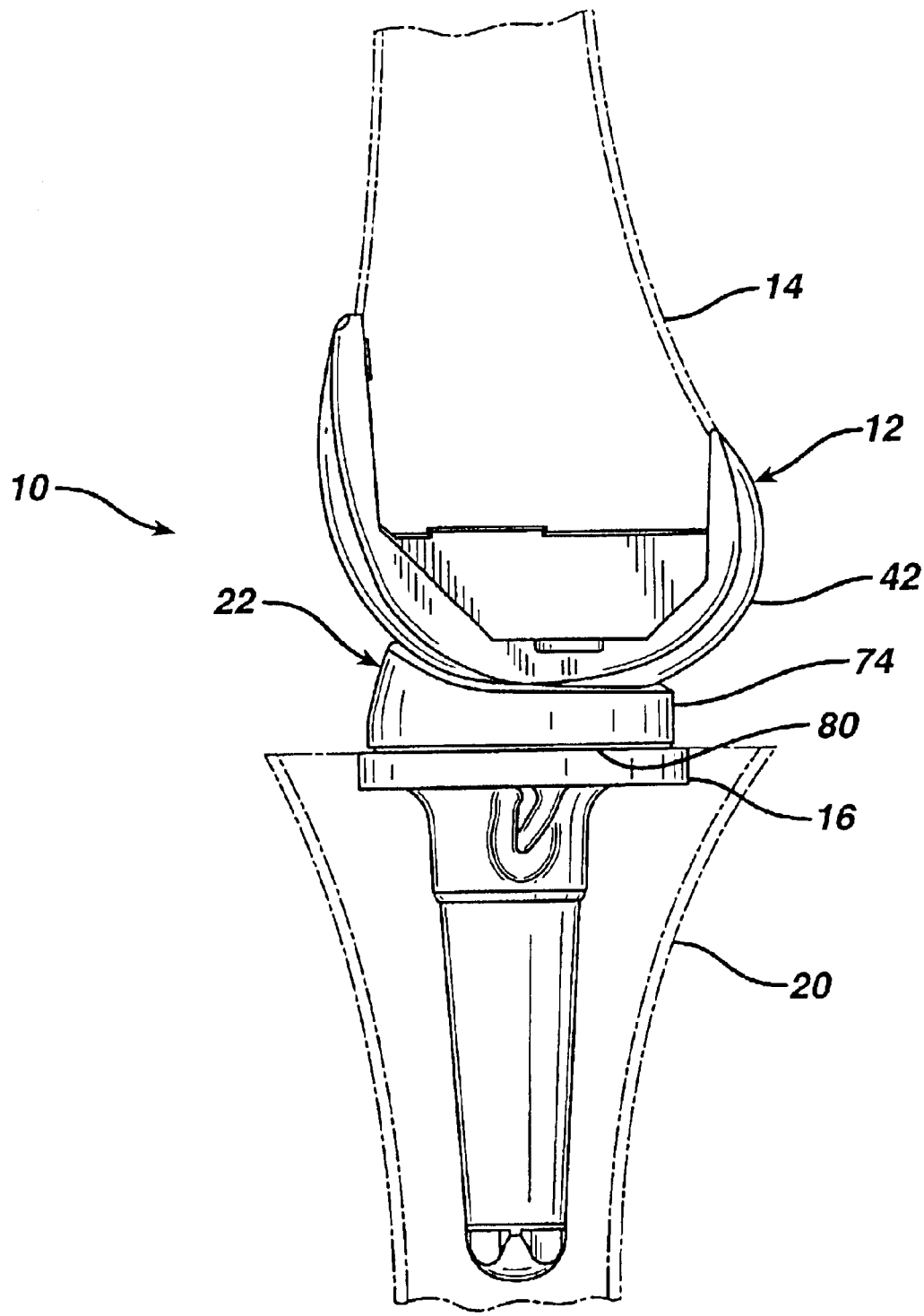
FIG. 3 is a side view of the assembly shown in FIGS. 1 and 2 implanted in a bone, shown in phantom view.
Figure 4:
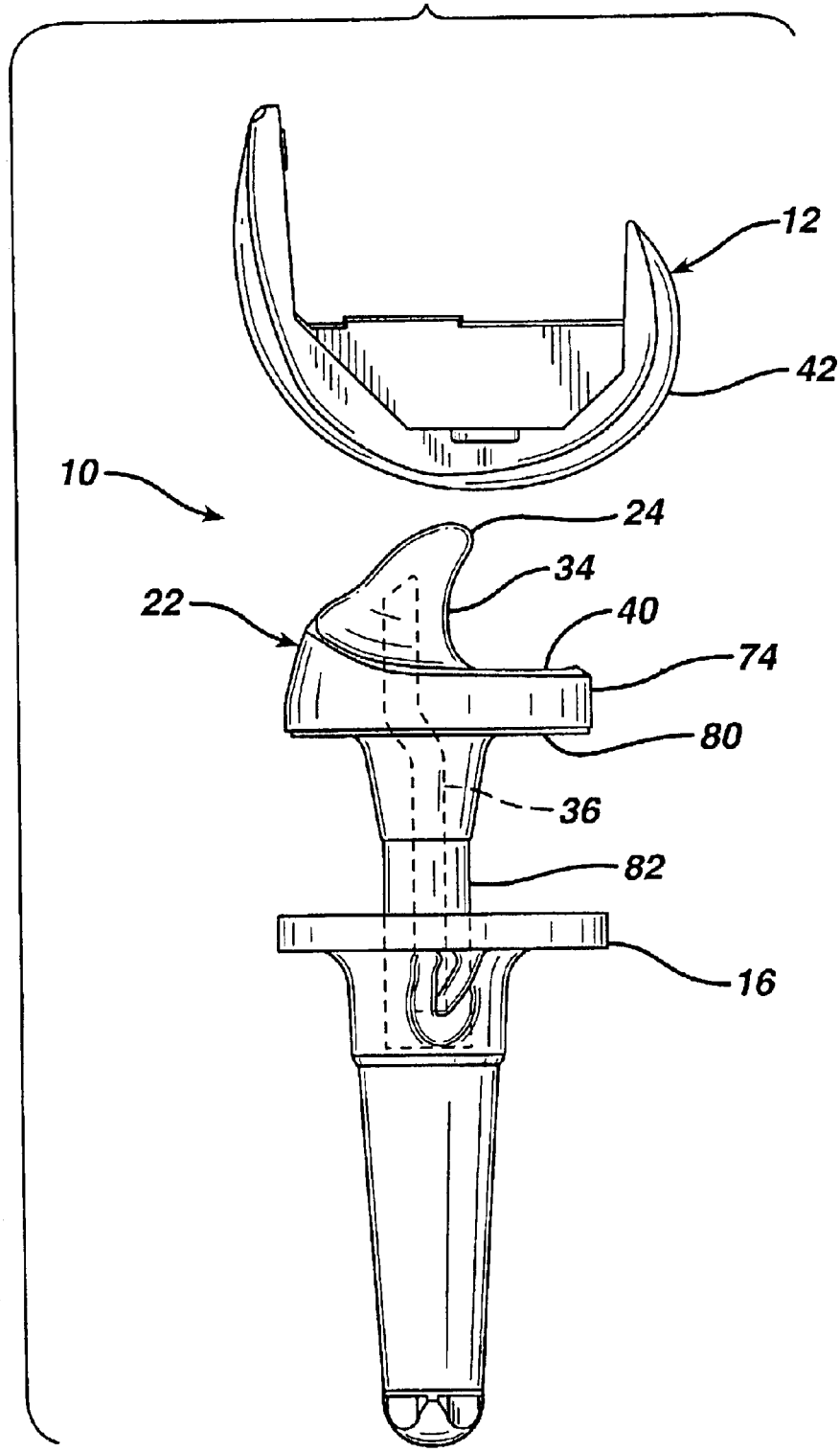
FIG. 4 is an exploded side view of the prosthesis of FIG. 1, showing the plastic bearing component partially removed from the tibial platform.
Figure 5:
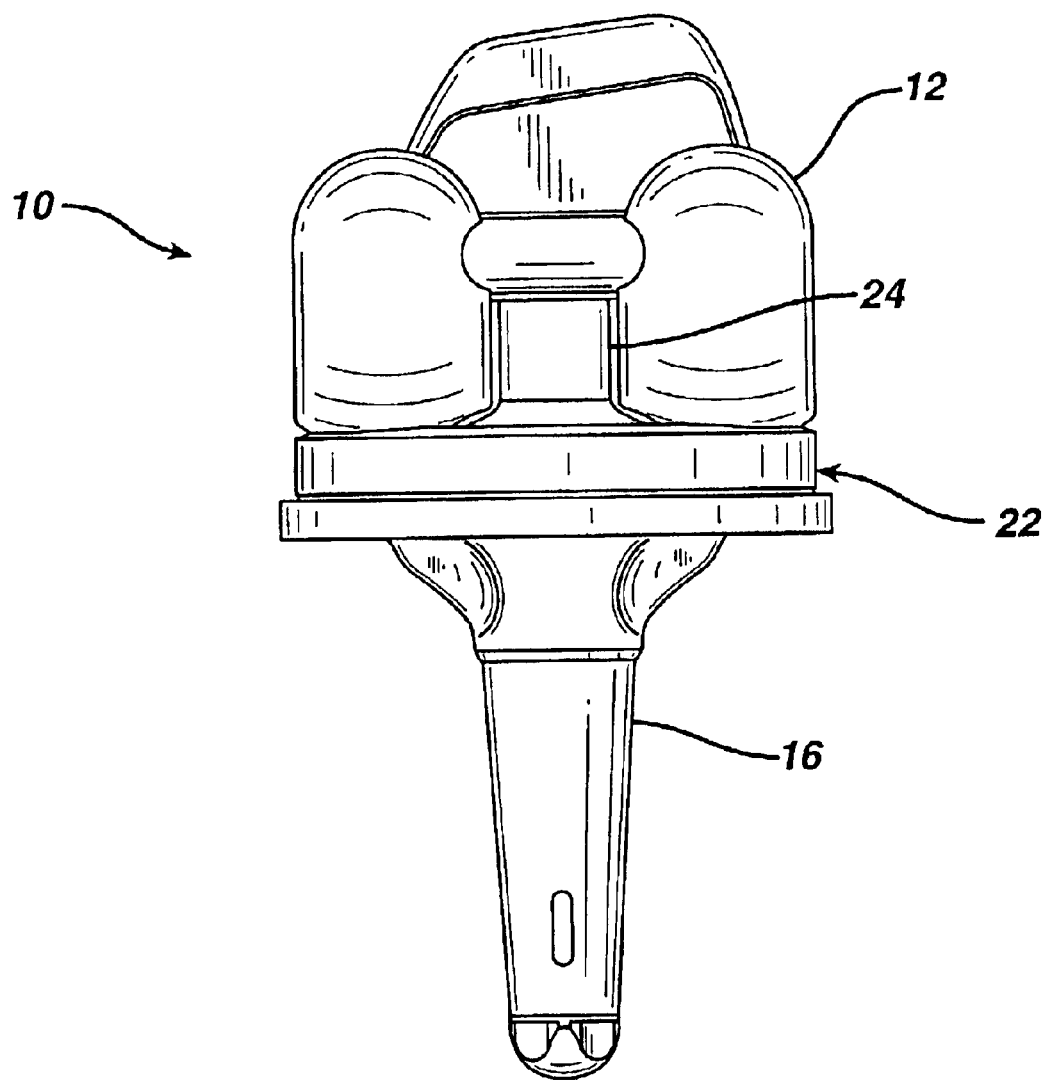
FIG. 5 is an elevation view from the posterior of FIG. 1.
Figure 6:
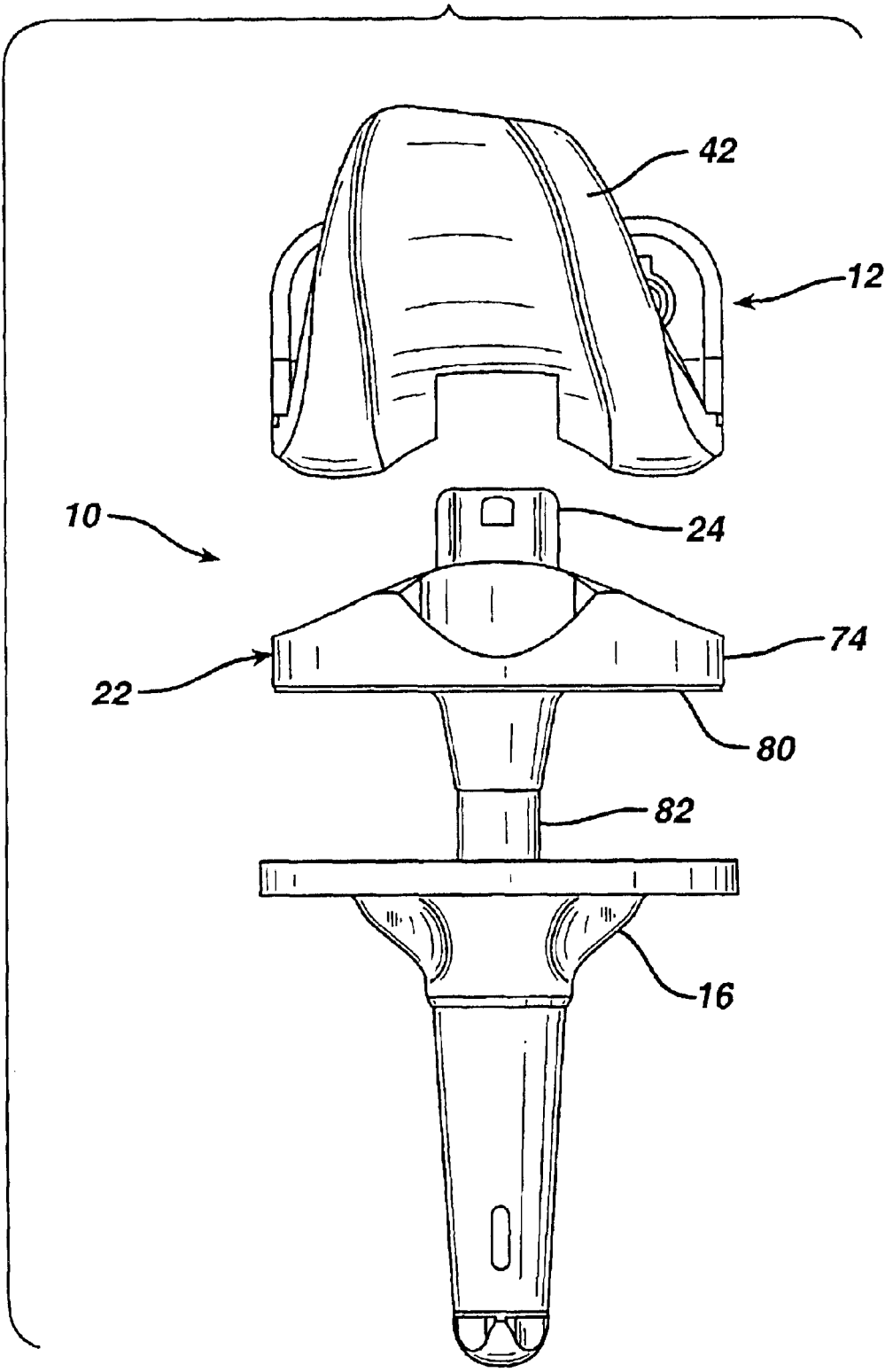
FIG. 6 is an exploded elevation view of FIG. 1 from the anterior showing the plastic bearing component partially removed from the tibial platform.
Figure 7:
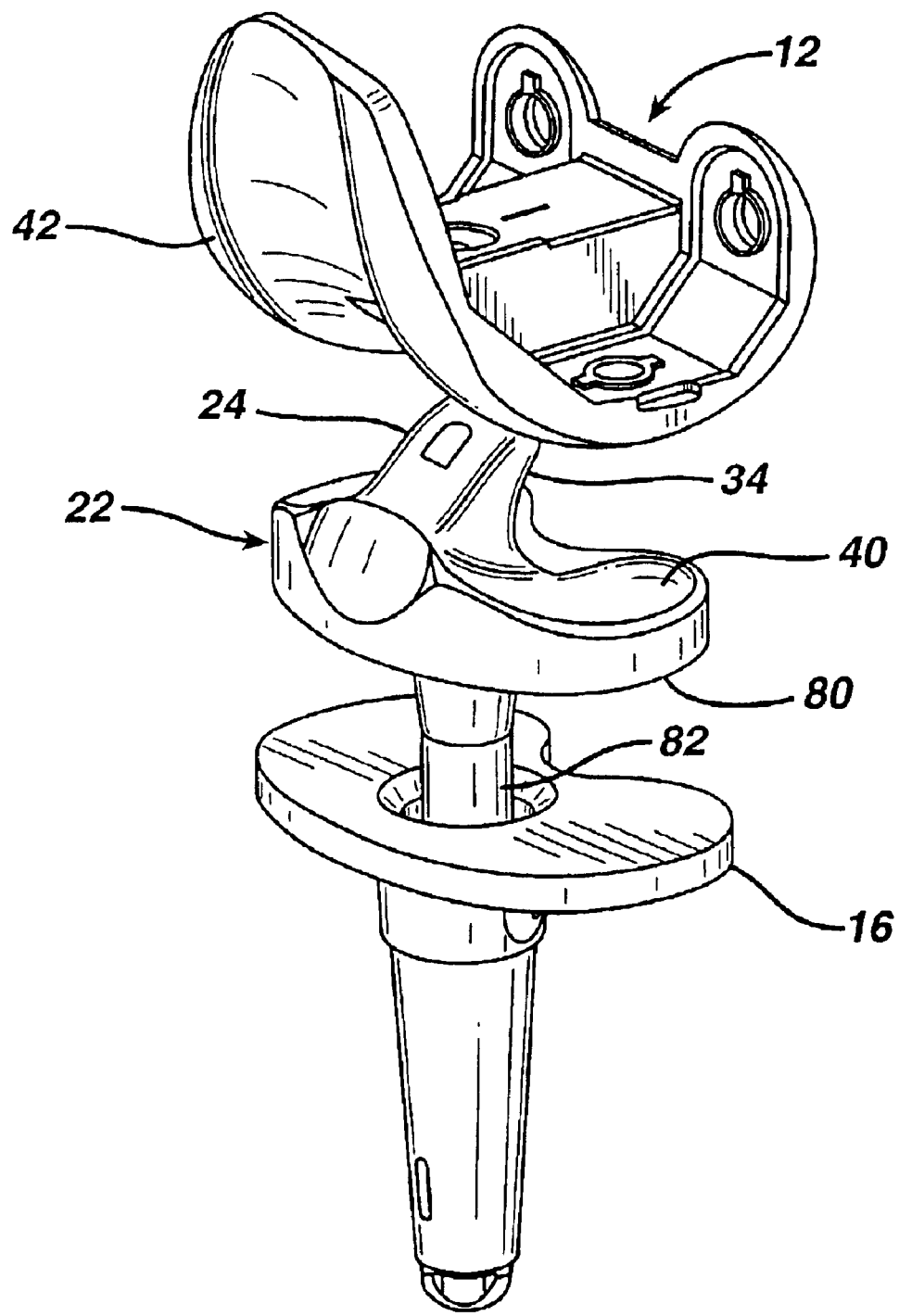
FIG. 7 is an exploded perspective view showing the plastic bearing component partially removed from the tibial platform.
Figure 8:
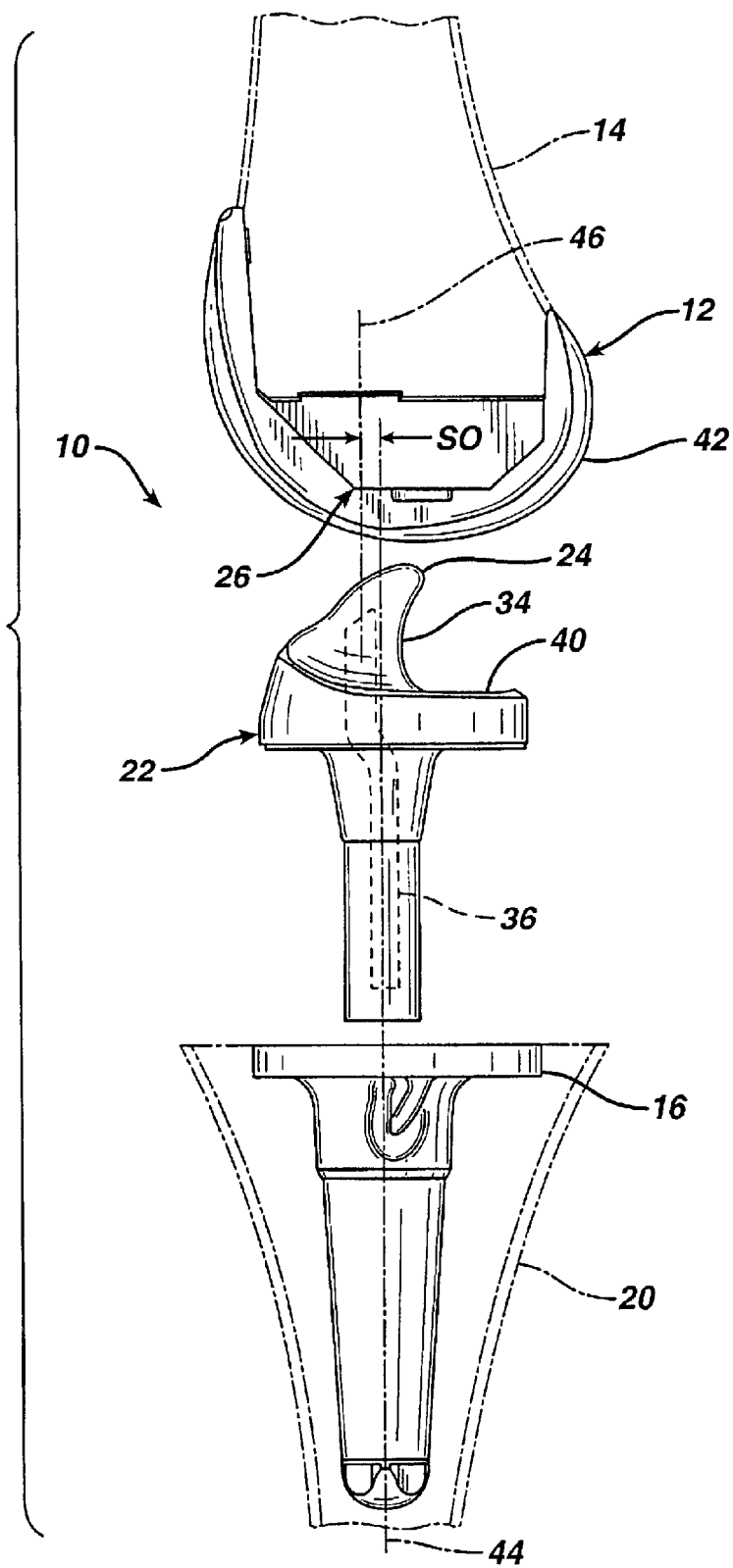
FIG. 8 is a fully exploded side view of FIG. 3 showing the plastic bearing component removed from the tibial platform.
Figure 9:
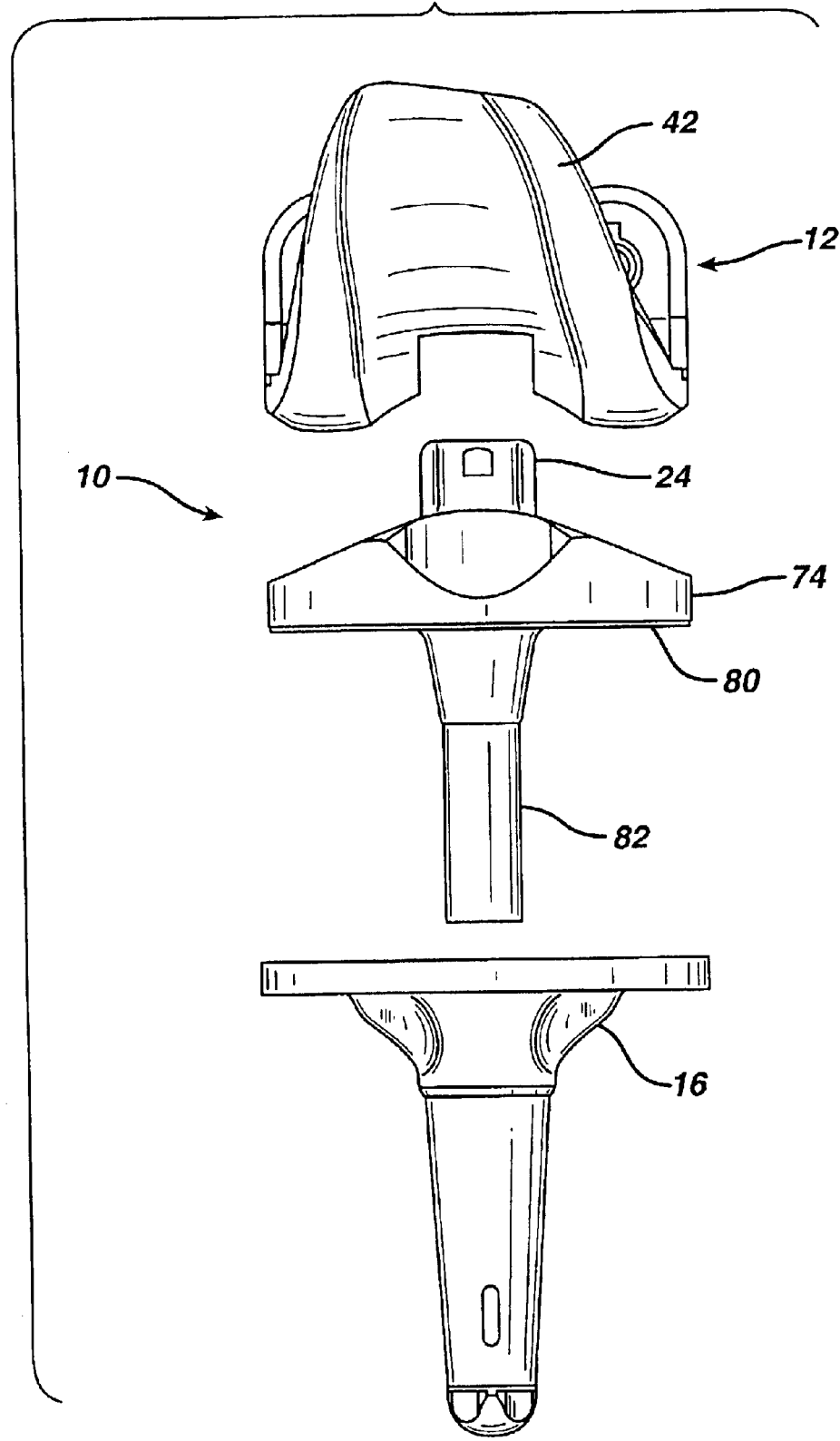
FIG. 9 is fully exploded elevation view from the anterior showing the plastic bearing component removed from the tibial platform.

According to the present invention and referring now to FIG. 8, a joint prosthesis in the form of knee prosthesis 10 is shown. The knee prosthesis 10 includes a femoral component or first component 12 for attachment to femur or first long bone 14. The prosthesis 10 further includes a tibial tray or second component 16 for attachment to tibia or second long bone 20. The femoral component 12 and the tibial component 16 are shown in greater detail in FIGS. 1–9 and 16–19. The femoral component 12 and the tibial component 16 are made of any suitable durable material which is biocompatible with the human anatomy. The femoral component 12 and the tibial component 16 may, for example, be made of a cobalt alloy, for example, cobalt-chromium-molybdenum, a titanium alloy, or be made of stainless steel.

The knee prosthesis 10 further includes a bearing component 22. The bearing component 22 is positionable between the femoral component 12 and the tibial tray 16. The bearing component 22 cooperates with the femoral component 12 and the tibial tray 16 to provide for the desired kinematics of the knee prosthesis.

The prosthesis as shown in FIGS. 1–9 and 16–19 are commonly referred to as a mobile bearing prosthesis or a mobile bearing knee. Such mobile bearing knees have been provided by DePuy Orthopaedics, Inc. under the trade name LCS since about 1977. Mobile bearing knees of this type are different than fixed bearing knees in that the tibial tray 16 and the bearing component 22 may be physically separated from each other. The use of mobile bearing knees may require that the patient have satisfactory cruciate ligaments and tendons necessary to maintain the proper relationship of the femoral component to the bearing component. In those cases where the cruciate ligaments are either severely damaged or have been sacrificed or removed during a knee surgery, provisions must be made within the prosthesis to constrain the femoral component with respect to the tibial tray to prevent subluxation or dislocation.

Figure 16:
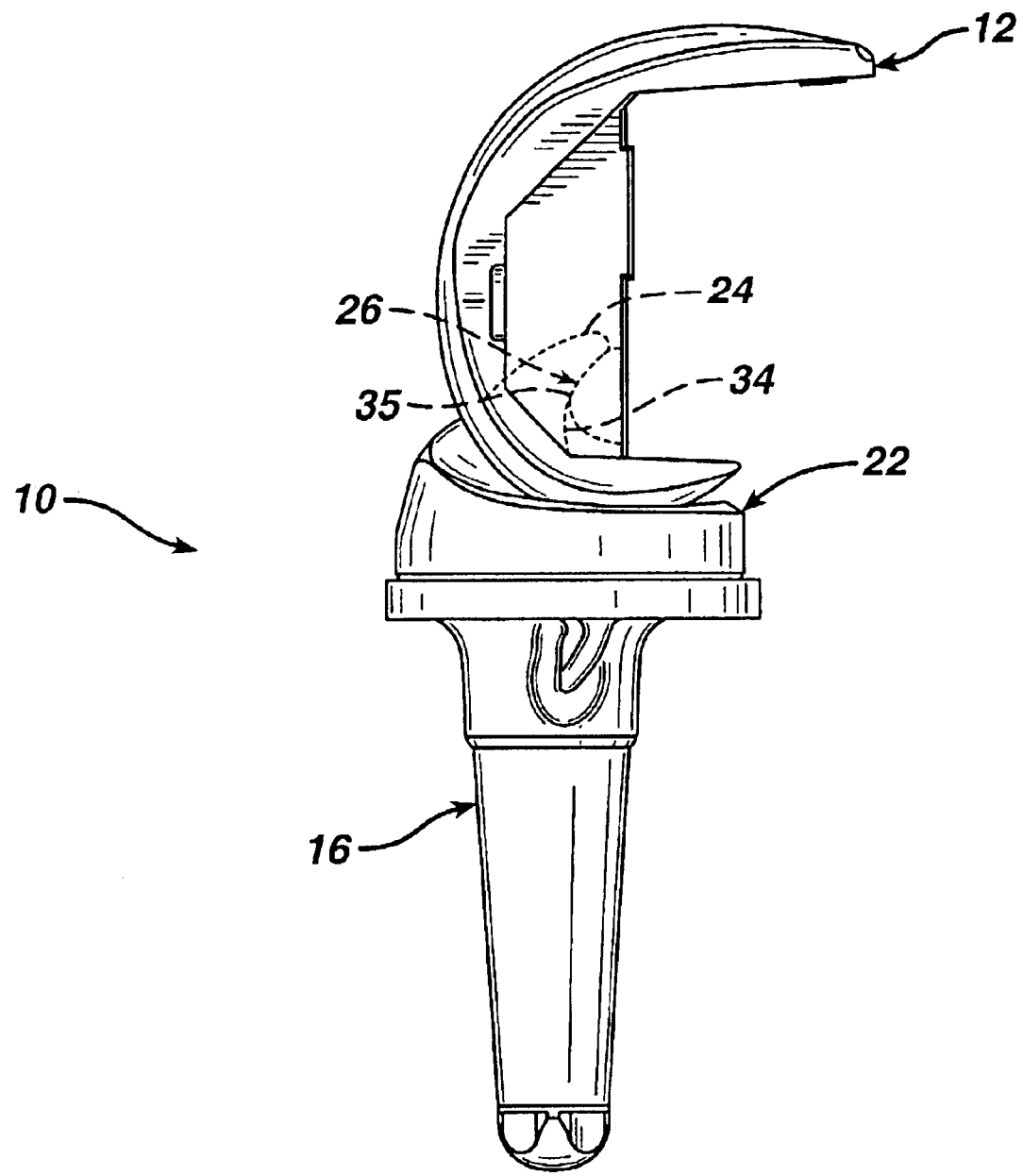
FIG. 16 is a side view of the assembly shown in FIGS. 1 and 2 showing the assembly in flexion.
Figure 17:
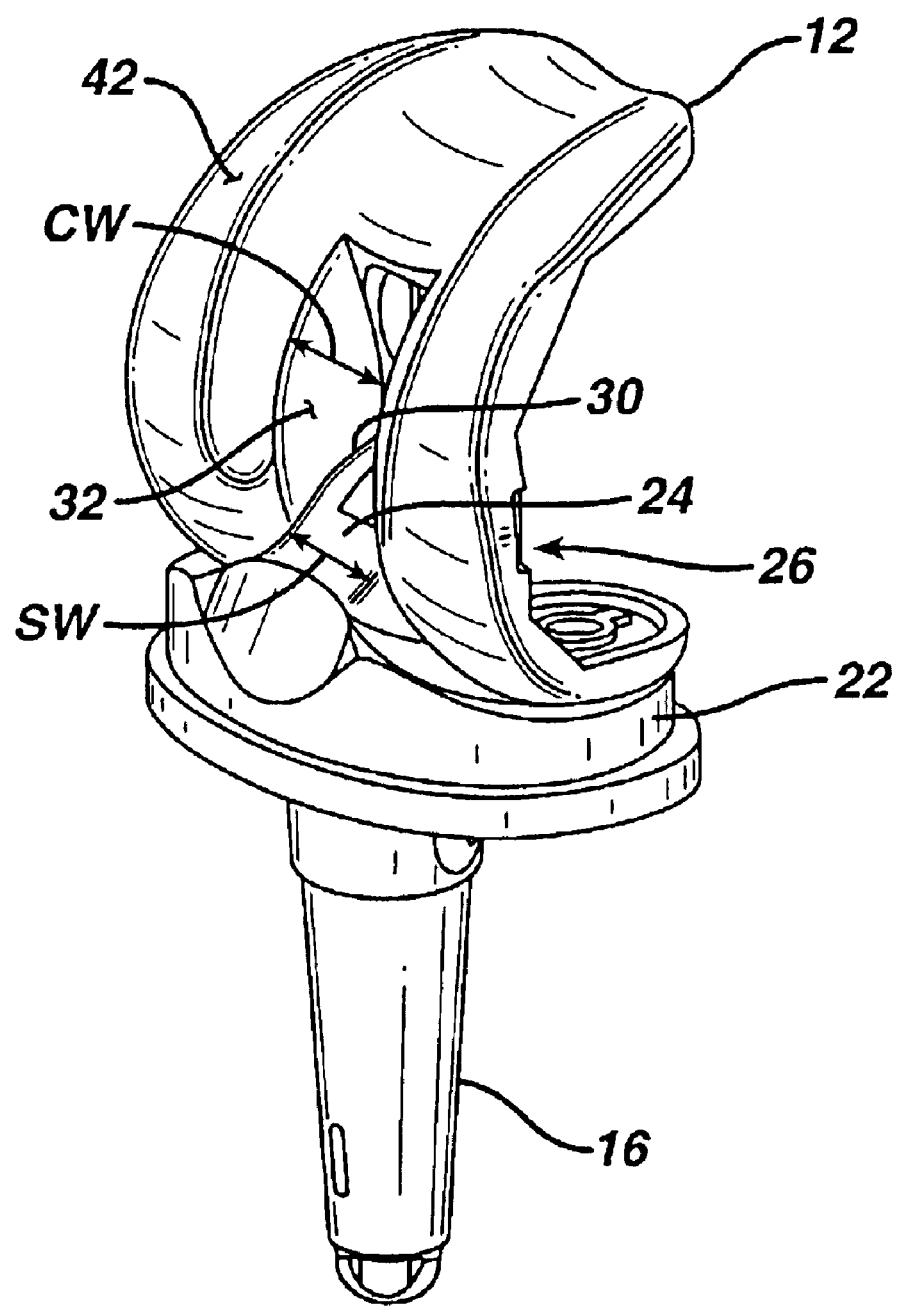
FIG. 17 is a perspective view of the knee system of FIG. 1 including the bearing component of the present invention showing the femoral component and the tibial component with the tibial bearing showing the knee system in flexion.
Figure 18:
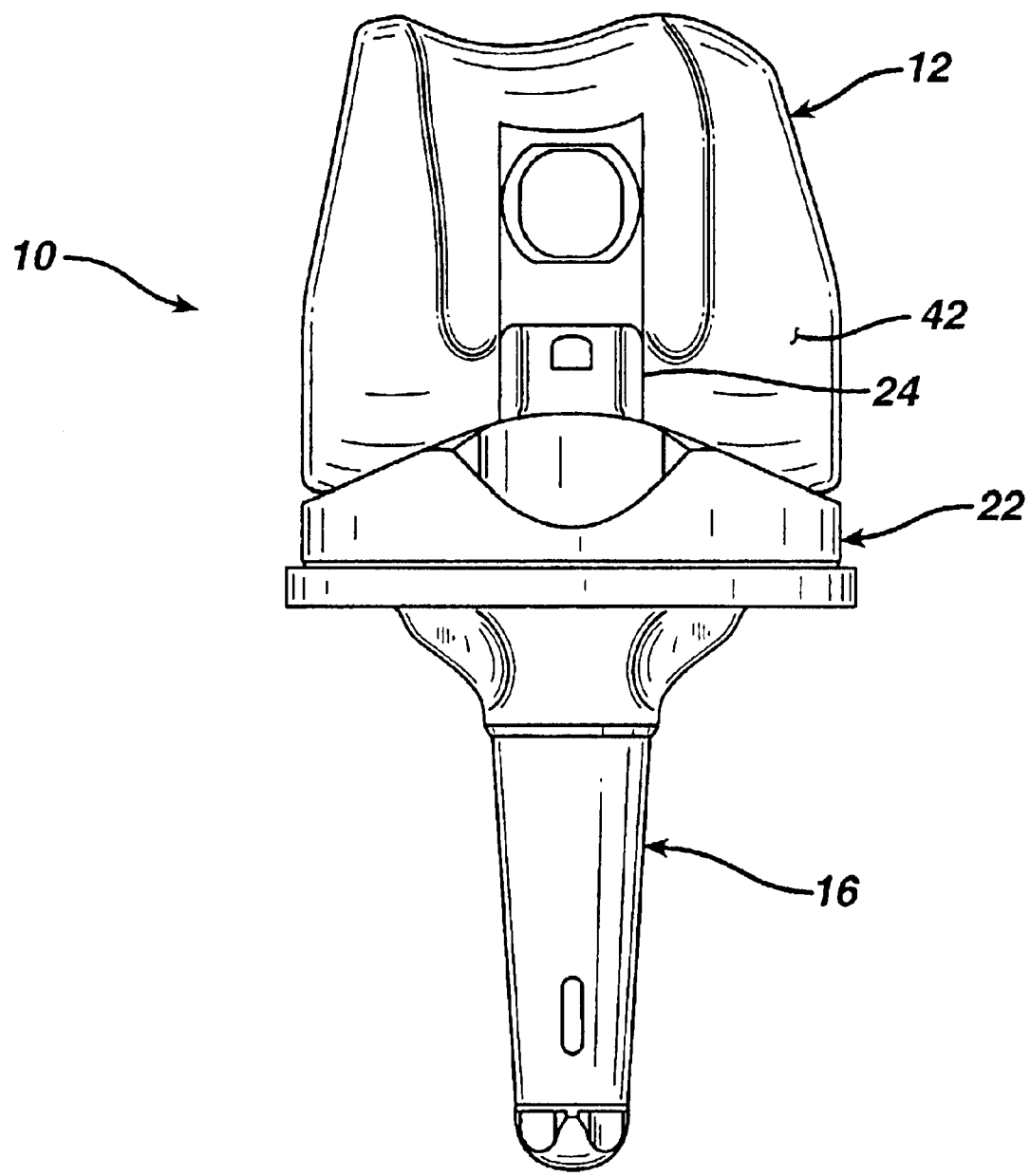
FIG. 18 is an elevation view from the anterior side of the assembly shown in FIGS. 1 and 2 showing the assembly in flexion.
Figure 19:
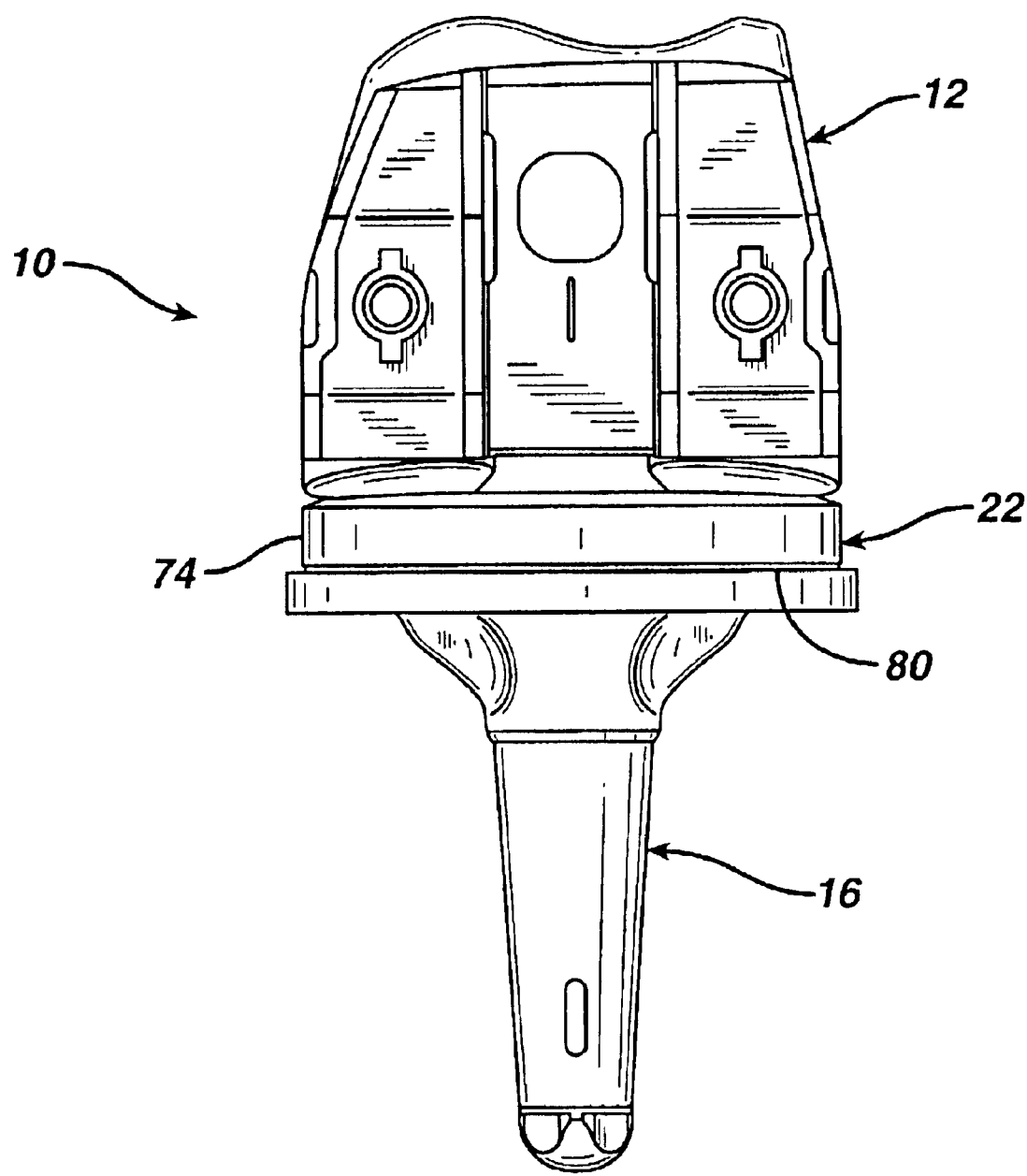
FIG. 19 is an elevation view from the posterior side of the assembly shown in FIGS. 1 and 2 showing the assembly in flexion.

Referring now to FIGS. 16 and 17, one solution to restraining the femoral component 12 with respect to the tibial tray is by the use of a mechanism in the form of a spine 24 located on the bearing component 22 which mates with cam 26 located on femoral component 12. As shown in FIGS. 16 and 17, to provide medial/lateral support for the knee prosthesis 10 preferably the femoral component 12 includes femoral face 30 which cooperate with spine faces 32 on the spine 24. The spine faces 32 define a spine width SW which is related to the femoral width CW defined by femoral faces 32 to allow for the desired kinematics in the medial lateral direction.

Referring now to FIG. 8, to provide anterior support the spine 24 includes a cam cooperating face or first peripheral region 34 with which the spine cooperating face 35 of the cam 26 cooperates (see FIG. 16). It should be appreciated that for patients in whom both the cruciate ligaments and the collateral ligaments are severely damaged, compromised or missing, the forces on the spine 24 both in the anterior/posterior direction and the medial/lateral direction can be quite severe.

Preferably, and as shown in FIG. 8, the bearing component 22 is made of a polymeric material, for example, polyethylene. Preferably, the bearing component 22 is made of UHMWPE. The bearing component 22 may be further processed to improve the wear properties of contact surface 40 of the bearing component. The contact surface 40 is that surface that is in contact with outer periphery 42 of the femoral component 12. Methods of improving the wear properties of UHMWPE include a process known as Gamma Vacuum Foil (GVF) as disclosed in U.S. Pat. No. 5,577,368 to Hamilton, et al, and a process known as the Marathon® process as disclosed in U.S. Pat. No. 6,017,975 and U.S. Pat. No. 6,242,507 to Saum, et al and in U.S. Pat. No. 6,228,900 to McKellop, et al. These patents are hereby incorporated herein by reference.

Referring again to FIG. 8, and according to the present invention, the bearing component 22 of the prosthesis 10 includes a first component or reinforcing component 36. The first component 36 serves to reinforce the bearing component 22 so that the spine 24 may withstand the forces that are present in the spine of the knee prosthesis, 10 when the cruciate ligaments and collateral ligaments cannot support the knee properly.

The first component 36 is preferably made of a higher modulus strength material than the polymer. For example, the first component 36 may be made of a metal, for example, a material compatible with the human anatomy, for example, stainless steel, a titanium alloy or a cobalt-chromium-molybdenum alloy.

Applicants have found that the desired kinematics of the knee during a full range of motion may require that an optimum design of the components that comprise a knee prosthesis for example those of FIG. 8, that may include an offset tibial tray 16 having a central pivot axis 44 which is not coincident with center line 46 of the spine 24 of the bearing component 22. Referring now to FIG. 10 and according to the present invention, the bearing component 22 of the prosthesis 10 includes the first component 36 which is designed to accommodate the fact that centerline 44 of the central pivot stem of the tibial tray 16 is offset from centerline 46 of the spine 24 (see FIG. 8). Thus as shown in FIG. 10, the first component 36 is designed with a first centerline 50 which is not coincident with second centerline 52. As shown in FIGS. 8 and 10, the first centerline 50 of the first component 36 is coincident with central pivot stem centerline 44 of tibial tray 16. Similarly the second centerline 52 of the first component 36 is coincident with the centerline 46 of the spine 24.

Continuing to refer to FIG. 10, the first component 36 includes a first portion 54 which defines the first centerline 50 thereof. The first component 36 further includes a second portion 56 thereof which defines the second centerline 52 thereof. The first centerline 50 and the second centerline 52 are non-coincidental.

As shown in FIG. 10, the first centerline 50 may be parallel and spaced from the second centerline 52. It should be appreciated, however, that the first centerline 50 and the second centerline 52 may, in fact, be skewed or converging or diverging. As shown in FIG. 10, however, the first centerline 50 and the second centerline 52 are separated and offset a distance CO which is similar to the offset SO between the centerline of 46 of spine 24 and the centerline 44 of the tibial tray 16 (see FIG. 8).

As shown in FIG. 10, the first component 36 includes a connecting portion 60 positioned between first portion 54 and second portion 56. The connecting portion 60 may have any suitable shape but preferably for strength and simplicity the connecting portion 60 is an arcuate portion. In such a configuration, the shape of the connecting portion 60 is defined by a pair of radii, R1 and R2 which may, for example, be similar.

While it should be appreciated that the first component 36 may have any suitable shape capable of providing for support with a pair of offset centerlines, it should be appreciated that for simplicity and as shown in FIG. 10 the first component 36 may have a uniform cross section. For example, the cross section of the first component may be square, triangular, hexagonal or as shown in FIG. 10A may be circular. A circular cross section may provide for optimum bending strength in a variety of directions for a given weight or size of the first component 36.

The first component 36 may be hollow or as shown in FIG. 10 may be made of a generally solid material. Due to space constraints, the first component 36 may be solid, as shown in FIG. 10.

As can be readily apparent by the FIGS. 8 and 10 in particular, the bearing component 22 including the first component 36 may be made by a number of methods but cannot simply and easily be made by first making the bearing component 22 and then preparing an opening or conduit for installing the first component 36 therein. Therefore, typical methods of providing a reinforcing rod to a bearing component 22 in the form of drilling a hole in the bearing component 22 and inserting a straight cylindrical rod therein is not possible.

Figure 12:
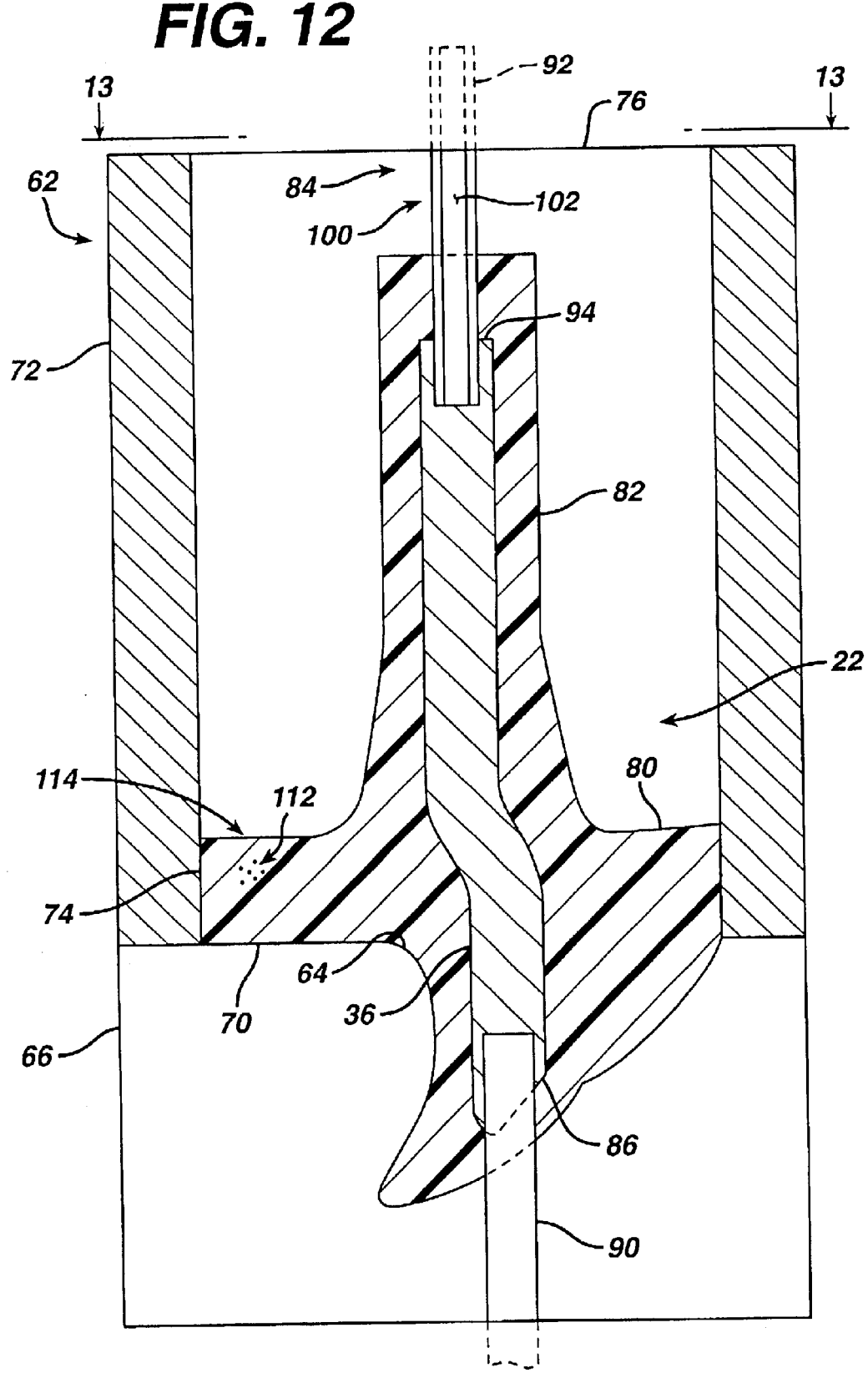
FIG. 12 is a plan view of the reinforcing rod of FIG. 10 located in a molding die shown partially in cross section for use in manufacturing the bearing component for the prosthesis of the present invention showing the molding die in greater detail.
Figure 13:
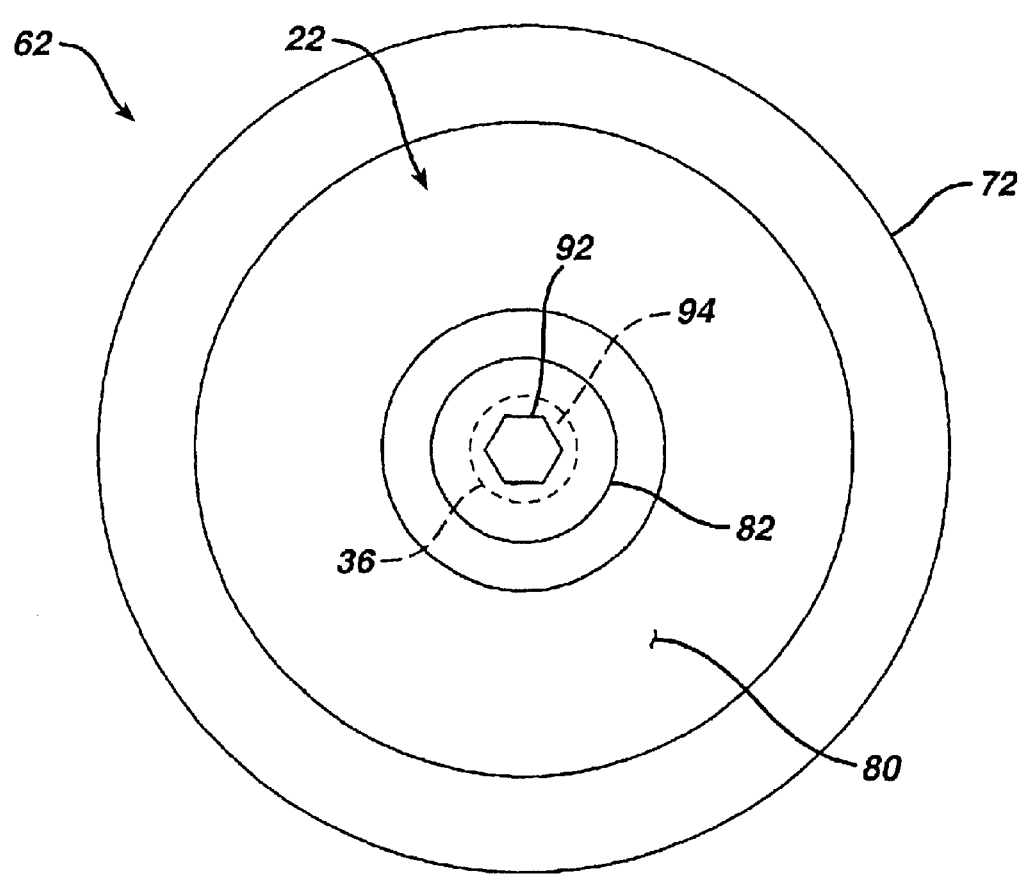
FIG. 13 is a bottom view of the molding die of FIG. 12.

Therefore, according to the present invention and referring to FIGS. 11, 12 and 13, the bearing component 22 is preferably made by a molding process, for example, a compression molding process or any molding process by which polymer may be processed. Referring to FIGS. 11, 12 and 13, the bearing component 22 is preferably made in molding die 62. While the bearing component 22 may be manufactured utilizing any suitable molding technique preferably and as shown in FIG. 12, the molding die 62 is for use with direct compression molding. Plastic powder is placed into the molding die 62, the die is closed and pressure is applied to compress, heat, and cause flow of the plastic to conform to the cavity shape.

The molding die 62 is made in a shape including an inner forming surface 64 which is made in the shape of the final finished bearing component 22. Preferably the inner forming surface 64 is sized to allow for appropriate shrinking dimensions as is known in the art.

The molding die is made in several pieces. Typically, a base or bottom mold 66 is utilized to form articular surface 70 of the bearing component 22. The molding die 62 also includes a body or side mold 72. The body 72 is utilized to form the curved lateral surfaces 74 of the bearing component 22. Also, the molding die 62 further includes a plunger assembly 76. The plunger assembly 76 is utilized to form bottom bearing surface 80 and the rotating shaft or second peripheral region 82. One mold may be used to obtain varying thicknesses of the tibial bearing component 22.

In order to manufacture the bearing component 22 according to the present invention, the molding die 62 is modified to support first component 36 in the form of, for example, a reinforcing rod.

Preferably, and as shown in FIG. 12, reinforcing rod 36 is position spaced from the inner forming surface 64. Preferably, and as shown in FIG. 12, the reinforcing rod 36 is kept spaced from the inner forming surface 64 by use of an orientation feature 84. The orientation feature 84 is utilized to space or position the reinforcing rod 36 within the molding die 62 as initially designed to provide the offset between the spine and distal stem of bearing component 22. The orientation feature or support system 84 may support or secure the first component of 36 at any suitable position on the first component 36. For simplicity and as shown in FIG. 12, the orientation Ser. No.10/154,869 feature 84 may be located on first end 86 of the reinforcing rod 36.

The orientation feature 84 may include a sole positioning member which interacts with first end 86 of the reinforcing rod 36. If the positioner is located only on one end and the rod is held at that one end, that portion of the die, including the positioner either at the base or bottom mold 66 or the plunger or top mold 76, must provide rigid temporary attachment of the reinforcing rod 36 to the orientation feature 84.

The positioner 84 may include a sole positioning member which interacts with first end 86 of the reinforcing rod 36. If the positioner is located only on one end and the rod is held at that one end, that portion of the die, including the positioner either at the base or bottom mold 66 or the plunger or top mold 76, must provide rigid temporary attachment of the reinforcing rod 36 to the positioner 84.

While the present invention may be practiced utilizing a sole positioner located on one end of the reinforcing rod 36, such a configuration may have some problems in that the tolerance between the positioner and the reinforcing rod may be such that the accuracy of the position of the reinforcing rod 36 within the molding die 62 may not be sufficiently accurate resulting in the misposition of the reinforcing rod 36 within the finished first component 36.

Misposition may occur either in the anterior/posterior or medial/lateral direction. Additionally, the reinforcing pin 36 may be rotationally mispositioned with respect to the superior spine and distal stem.

Preferably, thus, and as shown in FIG. 12, the positioner 84 is in the form of a first positioner 90 located at the first end 86 of the reinforcing rod 36 and a second positioner 92 located at second end 94 of the reinforcing rod 36. If the reinforcing rod 36 is held at both the first end 86 and the second end 94 of the rod 36, then one end, for example, first end 86 must be a rigid temporary attachment and the other end for example, second end 94 or second positioner 92 must be a sliding temporary attachment. A sliding temporary attachment is necessary as the two ends of the molding die approach and separate from each other during each molding cycle. Additionally, the sliding temporary attachment must provide for rotational alignment to obtain the optimal position of the reinforcing rod 36 in the spine by allowing equal polymeric material around the reinforcing rod 36.

To improve the accuracy of the positioning of the reinforcing rod 36 within the molding die 62, optionally, the molding die may include an orientation feature 100 to optimally angularly orient the reinforcing rod 36 with respect to the inner forming surface 64 and eventually the first component 36. The orientation feature 100 may, for example, be included with the positioners 90 and 92 and may, as shown in FIG. 12, be in the form of flat 102 located on the second positioner 92. As shown in FIG. 12, the orientation feature 100 is in the form of six equally spaced flats. Therefore, the positioner 84 and the orientation features are in the form of a hexagonal rod. An additional flat may help fine tune the position within the mold.

Referring again to FIG. 10, preferably, the reinforcing rod 36 includes positioning features in the form of, for example, first recess 104 which is located on first end 86 of the rod 36 and second recess 106 which is located on second end 94 of the rod 36. The first recess 104 matingly receives the first positioner 90 while the second recess 106 receives the second positioner 92 (see FIG. 11). Preferably, and as shown in FIG. 10, the second recess 106 includes a recess flat 110 which mate with flat 102 on second positioner 92.

Referring again to FIG. 12, plastic powder 112 is added in the proper amount into cavity 114 of the molding die 62. The molding die 62 is closed by the positioning of the plunger assembly or top mold 76 over the body or side mold 72 of the molding die 62.

The bearing component 22 is fully formed by subjecting the molding die 62 to the well known conditions of pressure and temperature required to consolidate the powder 112. After appropriate cooling, the molding die 62 is opened by the removal of the plunger assembly or top mold 76 from the body or side mold 72. The bearing component 22, including the reinforcing rod 36, is then removed from the cavity 114 of the molding die 62. After proper cleaning, and additional powder 112 is added to the cavity 114 and the process is repeated in order to obtain a second component.

Figure 15:
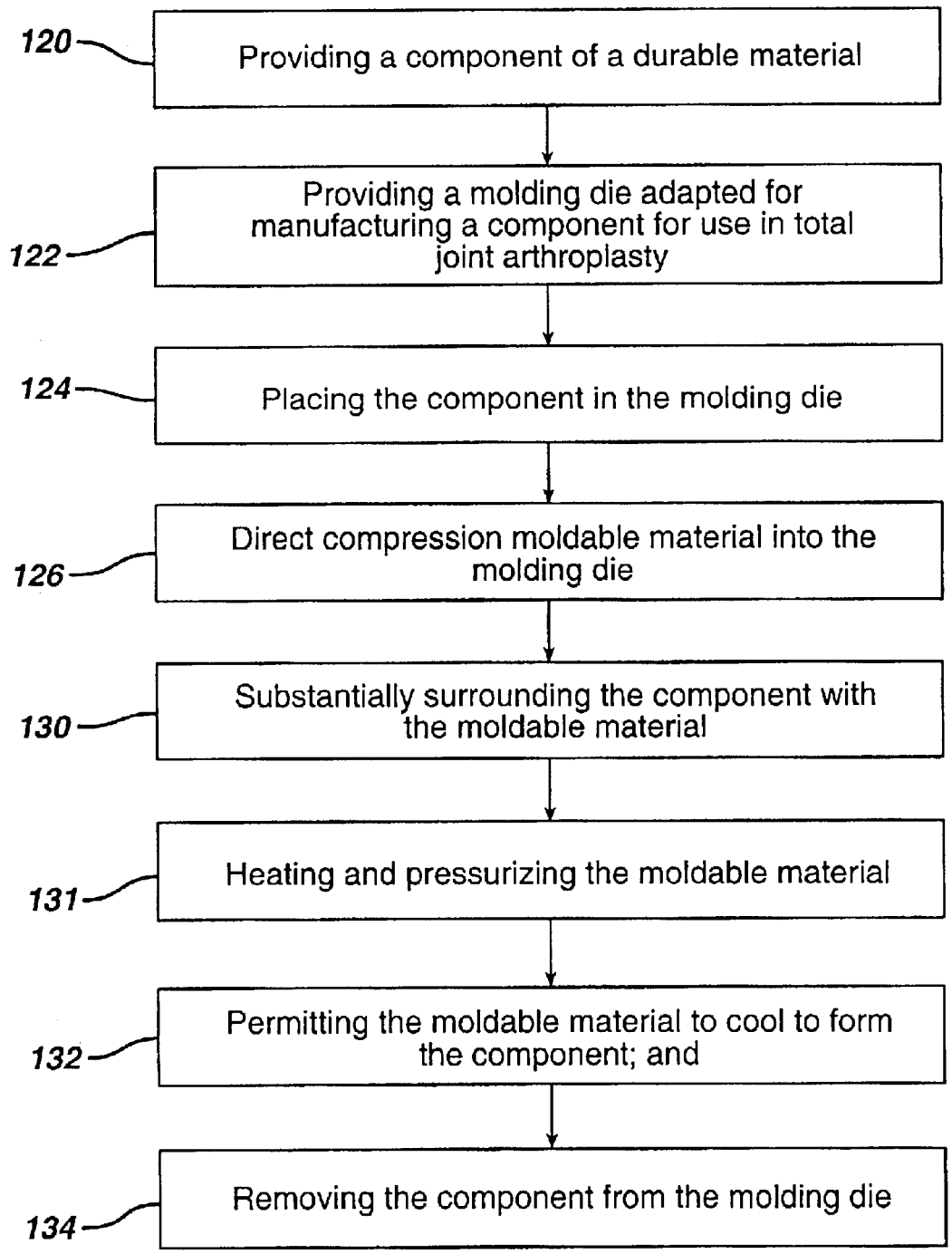
FIG. 15 is a process flow chart for a method of manufacturing the prosthesis component of FIG. 16.

Referring now to FIG. 15, a process for molding a bearing component with a reinforcing rod is described more fully. First step 120 of the process described in FIG. 15, is the step of providing a component of a durable material. The durable material may, for example, be in the form of cobalt-chromium-molybdenum, stainless steel alloy or titanium and its alloys. The component may be in the form of, for example, an elongated member, for example, a rod. The rod as described in the present invention is in the form of a bent rod or a rod having two substantially linear portions with the portions being skewed or non-collinear with respect to each other.

Second step 122 of the process, as described in FIG. 15, is the step of providing a molding die adapted for manufacturing a component for use in total joint arthroplasty.

Third step 124 in the process is the step of placing the reinforcing component into the molding die in a desired position.

Fourth step 126 of the process is placing moldable material powder into the molding die. Fifth step 130 in the process for making a bearing component is the step of substantially surrounding the component with moldable material. Sixth step 131 of the process is the step of heating and pressurizing the mold, thus the moldable material. Seventh step 132 of the process is the step of permitting the moldable material to cool to form the component and eighth step 134 of the process is the step of removing the component from the molding die.

Figure 14:
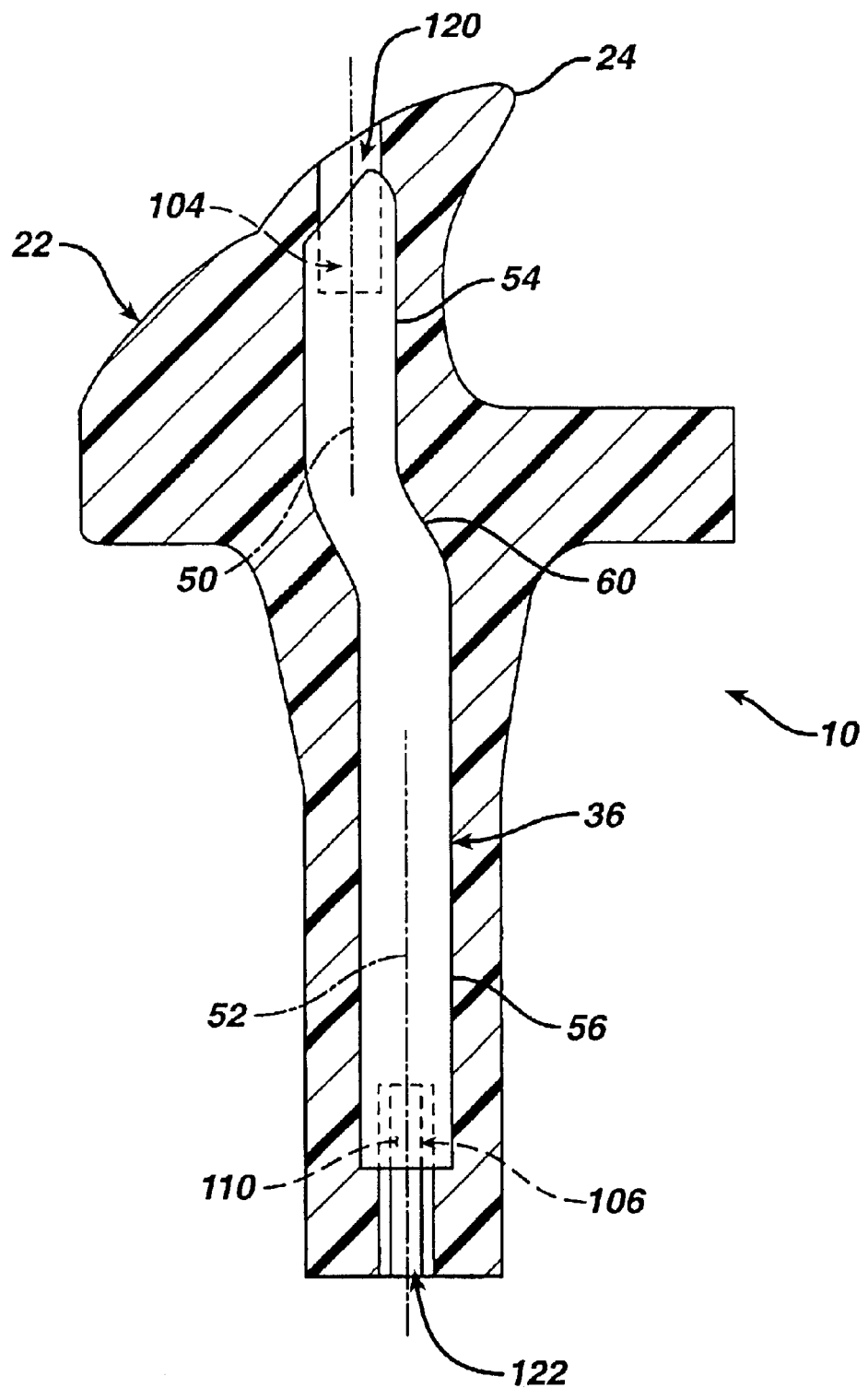
FIG. 14 is a partial section plan view of the bearing component made from the reinforcing rod of FIG. 10 utilizing the molding die of FIG. 12.

Referring to FIG. 14, since the prosthesis 10 including the bearing component 22 will be implanted into the human body, it is essential that the prosthesis 10 including the bearing component 22, be sterilized. Several effective methods of sterilization are possible for the prosthesis 10 including the bearing component 22. For example, the bearing component 22 may be sterilized by subjecting the bearing component 22 to gamma irradiation. The subjection of the bearing component 22 to gamma irradiation may lead to the presence of free radicals within the polymer or polyethylene with which the bearing component 22 is typically manufactured. The presence of free radicals within the bearing component 22 may lead to early degradation of the bearing component 22 through an oxidation process.

To minimize the negative effect of the free radicals generated from gamma sterilization, the bearing component 22 preferably is barrier packaged in vacuum or inert gas to keep the oxygen out and also to trap hydrogen gas generated by the sterilization process inside the package. Such treatment precludes or reduces the oxidation of the bearing insert and sufficient sterilization for the bearing component 22.

Alternatively, another method of sterilization in addition to gamma sterilization, is gas plasma sterilization. Gas plasma sterilization is predominantly a surface sterilizing technology. The ability of gas plasma sterilization has an undetermined ability to sterilize internal surfaces, which have limited exposure or connection to the outer surfaces of the component.

Referring now to FIG. 14, the bearing component 22 is shown having been molded on the molding die 62 (see FIGS. 12 & 13). In order that the first positioner 90 and the second positioner 92 may be removed from the cavity 114 and from the bearing component 22 when it is removed from the cavity 114 of the molding die 62, the bearing component 22 includes a first exposed component opening 120 located in line and above the first recess 104 of the reinforcing rod 36. Likewise, the bearing component 22 further includes a second exposed component opening 122 extending outwardly from the second recess 106 of the reinforcing rod 36. The first bearing component 120 and the second bearing component opening 122 provide for access to the reinforcing rod 36 from the outside of the bearing component 22.

By utilizing the non-linear reinforcement component of the present invention, a knee may be provided with improved load carrying capacity in the anterior/posterior and medial/lateral directions for the spine and cam mechanism in situations in which the center line of the insert which rotationally engages the tibial tray and the superior spine portion which engages the cam of the femoral component are not in the same plane. In such situations where these planes are different, the kinematics of the knee may be improved.

By providing a non-linear reinforcing component to the tibial bearing insert, the non-linear support rod may be properly positioned within the tibial bearing insert to optimize the load transfer mechanism through the spine.

By providing a tibial bearing insert including a non-linear support including an orientation feature, the non-linear support may be adjusted with respect to the tibial bearing insert during the manufacturing of the tibial bearing insert.

Although the present invention and its advantages have been described in detail, it should be understood that various changes, substitutions, and alterations can be made therein without departing from the spirit and scope of the present invention as defined by the appended claims.

What is claimed is:

1. A joint prosthesis, comprising:
a first component for cooperation with a long bone;
a second component for cooperation with a second long bone; and
a bearing component positionable between said first component and said second component and cooperable therewith, said bearing component including a reinforcing component having a first portion defining a first centerline thereof and having a second portion thereof defining a second centerline thereof, said first centerline and said second centerline being non-coincidental and a polymeric material surrounding the reinforcing component and molded thereto, the bearing component defining a first peripheral region adjacent the first portion of the reinforcing component and defining a second peripheral region adjacent the second portion of the reinforcing component, the first peripheral region cooperating with said first component and the second peripheral region cooperating with said second component, wherein the reinforcing component comprises a rod having opposed substantially linear portions and a central arcuate portion, wherein the reinforcing component defines a holding feature theron for holding the reinforcing component when placing the polymeric material onto the reinforcing component.

2. A joint prosthesis comprising:
a first component for cooperation with a first long bone;
a second component for cooperation with a second long bone; and
a bearing component positionable between said first component and said second component and cooperable therewith, said bearing component having a reinforcing component including an arcuate portion thereof, a first end portion extending from the arcuate portion of the first component and a polymeric material substantially surrounding the arcuate portion of the reinforcing component and molded thereto, the bearing component defining a first peripheral region adjacent the first end portion of the reinforcing component and a second peripheral region adjacent the second end portion of the reinforcing component, the first peripheral region cooperating with said first component and the second peripheral region cooperating with said second component, wherein the reinforcing component comprises a rod having first and second substantially linear portions extending from the arcuate portion, wherein the reinforcing component defines a holding feature thereon for holding the reinforcing component when placing the polymeric material onto the reinforcing component.

3. A knee prosthesis, comprising:
a femoral component for attachment to a femur;
a tibial tray for attachment to a tibia; and
a bearing component, positionable between said femoral component and said tibial tray for cooperation with said femoral component and said tibial tray, said bearing component including a first component having a first portion defining a first centerline thereof and having a second portion thereof defining a second centerline thereof, the first centerline and the second centerline being non-coincidental and said bearing component including a polymeric material substantially surrounding the first component and molded thereto, the bearing component defining a first peripheral region adjacent the first portion of the first component and defining a second peripheral region adjacent the second portion of the first component, the first peripheral region cooperating with the femoral component and the second peripheral region cooperating with the tibial tray, wherein said tibial tray is rotationally cooperable with said being component, wherein the first component defines a holding feature thereon for holding the first component when placing the polymeric material onto the first component.

* * * * *